US012521139B2

(12) United States Patent
Zhao et al.

(10) Patent No.: US 12,521,139 B2
(45) Date of Patent: Jan. 13, 2026

(54) METHODS, INSTRUMENTS, AND SYSTEMS FOR TISSUE SEALING

(71) Applicant: Covidien LP, Mansfield, MA (US)

(72) Inventors: Jing Zhao, Superior, CO (US); David J. Van Tol, Boulder, CO (US); Keith W. Malang, Longmont, CO (US); Matthew S. Cowley, Frederick, CO (US)

(73) Assignee: Covidien LP, Mansfield, MA (US)

( * ) Notice: Subject to any disclaimer, the term of this patent is extended or adjusted under 35 U.S.C. 154(b) by 793 days.

(21) Appl. No.: 17/911,314

(22) PCT Filed: Feb. 21, 2022

(86) PCT No.: PCT/US2022/017141

§ 371 (c)(1),
(2) Date: Sep. 13, 2022

(87) PCT Pub. No.: WO2022/197403

PCT Pub. Date: Sep. 22, 2022

(65) Prior Publication Data

US 2024/0180579 A1 Jun. 6, 2024

Related U.S. Application Data

(60) Provisional application No. 63/161,730, filed on Mar. 16, 2021.

(51) Int. Cl.
*A61B 17/32* (2006.01)
*A61B 17/00* (2006.01)
(Continued)

(52) U.S. Cl.
CPC ...... *A61B 17/320092* (2013.01); *A61B 34/10* (2016.02); *A61B 90/361* (2016.02);
(Continued)

(58) Field of Classification Search
CPC ............ A61B 1/00006; A61B 1/00009; A61B 17/320092; A61B 18/1445;
(Continued)

(56) References Cited

U.S. PATENT DOCUMENTS 5,836,869 A 11/1998 Kudo et al.
8,764,749 B2 7/2014 McKenna et al.
(Continued)

FOREIGN PATENT DOCUMENTS

EP 3329874 A1 6/2018

OTHER PUBLICATIONS

International Search Report and Written Opinion received for PCT Application No. PCT/US2022/017141, mailed on May 30, 2022, 9 pages.

(Continued)

*Primary Examiner* — Mohamed G Gabr
*Assistant Examiner* — Khoa Tan Le

(57) ABSTRACT

An ultrasonic surgical system includes an ultrasonic instrument configured to seal a vessel and including an ultrasonically-activatable blade and a jaw member pivotably movable with respect to the blade, an endoscope configured to capture video data of a surgical site including the blade and the jaw member, and a processor connected to the endoscope. The processor is configured to process the video data to determine an angle between the blade and the jaw member, determine a desired energy level based on the angle, and provide the desired ultrasonic energy as a feedback to the ultrasonic instrument. The ultrasonic instrument performs a closed-loop control to maintain the desired ultrasonic energy.

13 Claims, 9 Drawing Sheets

(51) Int. Cl.
*A61B 34/10* (2016.01)
*A61B 90/00* (2016.01)

(52) U.S. Cl.
CPC .... *A61B 90/39* (2016.02); *A61B 2017/00137* (2013.01); *A61B 2017/00296* (2013.01); *A61B 2017/320075* (2017.08); *A61B 2017/320094* (2017.08); *A61B 2090/3937* (2016.02)

(58) Field of Classification Search
CPC ...... A61B 18/1482; A61B 2017/00137; A61B 2017/00296; A61B 2017/320075; A61B 2017/320094; A61B 2090/067; A61B 2090/3937; A61B 34/10; A61B 34/30; A61B 90/361; A61B 90/39
See application file for complete search history.

(56) References Cited

U.S. PATENT DOCUMENTS

| | | | |
|---|---|---|---|
| 2017/0215944 A1 | 8/2017 | Keffeler | |
| 2019/0200980 A1 | 7/2019 | Shelton, IV et al. | |
| 2019/0201018 A1 | 7/2019 | Shelton, IV et al. | |
| 2019/0201033 A1 | 7/2019 | Yates et al. | |
| 2019/0201040 A1 | 7/2019 | Messerly et al. | |
| 2019/0201042 A1 | 7/2019 | Nott et al. | |
| 2019/0201073 A1 | 7/2019 | Nott et al. | |
| 2019/0201080 A1 | 7/2019 | Messerly et al. | |
| 2019/0201081 A1 | 7/2019 | Shelton, IV et al. | |
| 2019/0201112 A1 | 7/2019 | Wiener et al. | |
| 2019/0201114 A1 | 7/2019 | Shelton, IV et al. | |
| 2019/0201115 A1 | 7/2019 | Shelton, IV et al. | |
| 2019/0201117 A1 | 7/2019 | Yates et al. | |
| 2019/0201122 A1 | 7/2019 | Shelton, IV et al. | |
| 2019/0201124 A1 | 7/2019 | Shelton, IV et al. | |
| 2019/0201126 A1 | 7/2019 | Shelton, IV et al. | |
| 2019/0201127 A1 | 7/2019 | Shelton, IV et al. | |
| 2019/0201128 A1 | 7/2019 | Yates et al. | |
| 2019/0201130 A1 | 7/2019 | Shelton, IV et al. | |
| 2019/0201140 A1 | 7/2019 | Yates et al. | |
| 2019/0274705 A1 | 9/2019 | Sawhney et al. | |
| 2019/0274706 A1 | 9/2019 | Nott et al. | |
| 2019/0274707 A1 | 9/2019 | Sawhney et al. | |
| 2019/0274708 A1 | 9/2019 | Boudreaux | |
| 2019/0274709 A1 | 9/2019 | Scoggins | |
| 2019/0274710 A1 | 9/2019 | Black | |
| 2019/0274711 A1 | 9/2019 | Scoggins et al. | |
| 2019/0274712 A1 | 9/2019 | Faller et al. | |
| 2019/0274714 A1 | 9/2019 | Cuti et al. | |
| 2019/0274716 A1 | 9/2019 | Nott et al. | |
| 2019/0274719 A1 | 9/2019 | Stulen | |
| 2019/0274750 A1 | 9/2019 | Jayme et al. | |
| 2019/0274752 A1 | 9/2019 | Denzinger et al. | |
| 2019/0282292 A1 | 9/2019 | Wiener et al. | |
| 2019/0298398 A1* | 10/2019 | Wellman | A61B 17/282 |
| 2020/0078070 A1 | 3/2020 | Henderson et al. | |
| 2020/0078076 A1 | 3/2020 | Henderson et al. | |
| 2020/0078078 A1 | 3/2020 | Henderson et al. | |
| 2020/0078079 A1 | 3/2020 | Morgan et al. | |
| 2020/0078106 A1 | 3/2020 | Henderson et al. | |
| 2020/0078114 A1 | 3/2020 | Asher et al. | |
| 2020/0078118 A1 | 3/2020 | Henderson et al. | |
| 2020/0078120 A1 | 3/2020 | Aldridge et al. | |
| 2020/0100825 A1 | 4/2020 | Henderson et al. | |
| 2020/0100830 A1 | 4/2020 | Henderson et al. | |
| 2020/0100850 A1 | 4/2020 | Strobl | |
| 2020/0106220 A1 | 4/2020 | Henderson et al. | |
| 2020/0305945 A1 | 10/2020 | Morgan et al. | |
| 2020/0314569 A1 | 10/2020 | Morgan et al. | |
| 2021/0000555 A1 | 1/2021 | Shelton, IV et al. | |
| 2021/0338216 A1 | 11/2021 | Cox, Jr. et al. | |

OTHER PUBLICATIONS

European Examination Report for EP Application No. 22 709 120.4 mailed May 6, 2025 (4 pages).

* cited by examiner

METHODS, INSTRUMENTS, AND SYSTEMS FOR TISSUE SEALING

CROSS-REFERENCE TO RELATED APPLICATIONS

This application is a 371 National Stage Application of International Application No. PCT/US2022/017141, filed Feb. 21, 2022, which claims the benefit of U.S. Provisional Patent Application No. 63/161,730, filed Mar. 16, 2021, the entire contents of each of which are hereby incorporated herein by reference.

BACKGROUND

Technical Field

The present disclosure relates to methods, surgical instruments, and systems for sealing tissue. More particularly, the present disclosure relates to methods, instruments, and systems that perform closed-loop control to treat tissue, e.g., blood vessels.

Background of Related Art

Ultrasonic surgical instruments include ultrasonic transducers that vibrate attached end effectors, to seal and/or cut tissue due to heat imparted by rapid movements of the end effectors. Ultrasonic movements are controlled by closure of a jaw member and the extent of vibration, and multiple energy or lengths of tip displacement are used to seal or cut clamped tissue or cut tissue in contact with the end effector.

Open-loop control strategies, which control an end effector vibrating speed to follow a group of pre-defined set points, have been employed to treat different size tissues, e.g., vessels. However, since the size of the tissue is not known prior to treatment, open-loop control strategies cannot adjust the amount of delivered energy to balance activation time and surgical operation quality. Thus, there is a need for adaptive delivery of energy to ultrasonic instruments so that different sizes of tissue may be effectively treated.

SUMMARY

According to various aspects of the present disclosure, an ultrasonic surgical system includes an ultrasonic instrument configured to seal a vessel and including an ultrasonically-activatable blade and a jaw member pivotably movable with respect to the blade, an endoscope configured to capture video data of a surgical site including the blade and the jaw member, and a processor connected to the endoscope. The processor is configured to process the video data to determine an angle between the blade and the jaw member, determine a desired ultrasonic energy level based on the angle, and provide the desired ultrasonic energy level as a feedback to the ultrasonic instrument. The ultrasonic instrument performs a closed-loop control to maintain the desired ultrasonic energy level.

According to aspects of the present disclosure, a first marker is disposed on the blade, a second marker is disposed on the jaw member, a third marker is disposed near a pivot of the ultrasonic instrument.

According to aspects of the present disclosure, at least one additional marker is disposed near each of the first and third markers.

According to aspects of the present disclosure, the angle between the blade and the jaw member is determined based on the first, second, and third markers in the captured video data.

According to aspects of the present disclosure, the angle between the blade and the jaw member is further determined based on the first, second, and third markers and a fourth marker disposed on a shaft of the ultrasonic instrument.

According to aspects of the present disclosure, the processor is further configured to execute an artificial intelligence algorithm to process the video data.

According to further aspects of the present disclosure, the ultrasonic instrument includes a memory storing predetermined activation periods corresponding to angles between the jaw member and the blade. The angle together with the desired energy level is provided to the ultrasonic instrument. Supply of the energy is altered after an activation time corresponding to the angle has passed.

According to still further aspects of the present disclosure, the processor is further configured to control a velocity of the blade based on the desired ultrasonic energy level.

According to still further aspects of the present disclosure, the closed-loop control is a proportional-integral (PI) control, proportional-integral-derivative (PID) control, or a cascade of PI or PID controls.

According to various aspects of the present disclosure, a method for performing a closed-loop control to seal a vessel with an ultrasonic instrument includes receiving an activation signal from the ultrasonic instrument, which includes an ultrasonically-activatable blade and a jaw member pivotably movable with respect to the blade, capturing video data of a surgical site including the blade and the jaw member of the ultrasonic instrument, processing the video data to determine an angle between the blade and the jaw member, determining a desired ultrasonic energy level based on the angle, providing the desired ultrasonic energy level as a feedback to the ultrasonic instrument, and performing a closed-loop control to maintain the desired ultrasonic energy level.

According to aspects of the present disclosure, a first marker is disposed on the blade, a second marker is disposed on the jaw member, a third marker is disposed near a pivot of the ultrasonic instrument. The angle between the blade and the jaw member is determined based on the first, second, and third markers in the captured video data.

According to aspects of the present disclosure, the angle between the first and second jaw members is determined based on the first, second, and third markers in the captured video data.

According to further aspects of the present disclosure, the video data is processed by an artificial intelligence algorithm.

According to still further aspects of the present disclosure, predetermined activation times corresponding to angles between the blade and the jaw member are stored in a memory of the ultrasonic instrument. The angle together with the desired energy level is provided to the ultrasonic instrument. The method further includes altering the energy to the ultrasonic instrument after a predetermined activation time corresponding to the angle has passed.

According to still further aspects of the present disclosure, the method further includes controlling a velocity of the blade based on the ultrasonic energy level.

According to still further aspects of the present disclosure, the closed-loop control is a proportional-integral (PI) control, proportional-integral-derivative (PID) control, or a cascade of PI or PID controls.

According to various aspects of the present disclosure, a non-transitory computer-readable medium includes instructions stored thereon that, when executed by a computing device, cause the computing device to perform a method for performing a closed-loop control to seal a vessel with an ultrasonic instrument. The method includes receiving an activation signal from the ultrasonic instrument, which includes an ultrasonically-activatable blade and a jaw member pivotably movable with respect to the blade, capturing video data of a surgical site including the blade and the jaw member of the ultrasonic instrument, processing the video data to determine an angle between the blade and the jaw member, determining a desired ultrasonic energy level based on the angle, providing the desired energy level as a feedback to the ultrasonic instrument, and performing a closed-loop control to maintain the desired energy level.

BRIEF DESCRIPTION OF THE DRAWINGS

The present disclosure may be understood by reference to the accompanying drawings, when considered in conjunction with the subsequent, detailed description, in which.

DETAILED DESCRIPTION

Figure 1:
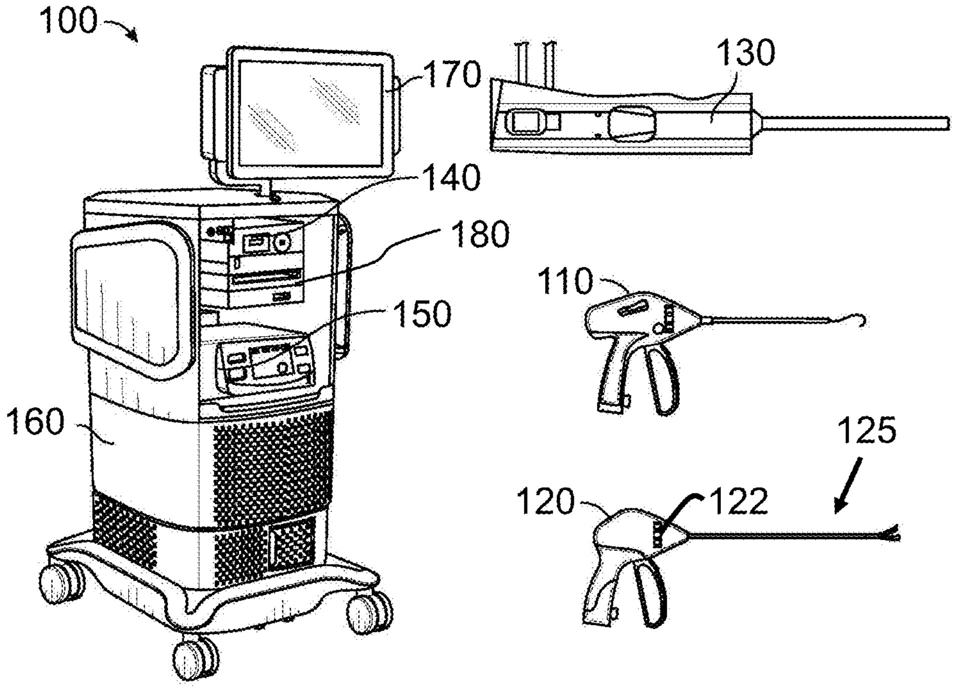
FIG. 1 is a perspective view of an energy-based surgical system according to various aspects of the present disclosure.

Aspects of the presently disclosed energy-based surgical system are described in detail with reference to the drawings, in which like reference numerals designate identical or corresponding elements in each of the several views. As used herein the term “distal” refers to the portion of the surgical instrument or component thereof that is closer to the patient, while the term “proximal” refers to the portion that is farther from the patient.

The term “application” may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, an Internet of things (IOT) device, a server system, or any programmable logic device.

In the following description, well-known functions or constructions are not described in detail to avoid obscuring the present disclosure in unnecessary detail. Those skilled in the art will understand that the present disclosure may be adapted for use with either an endoscopic instrument, a laparoscopic instrument, an open instrument, or as part of a robotic surgical system. It should also be appreciated that different electrical and mechanical connections and other considerations may apply to each particular type of instrument or system.

An energy generator according to the present disclosure may be used in monopolar and/or bipolar electrosurgical procedures, in ultrasonic procedures, and/or in other procedures in order to, for example, enable cutting, coagulation, ablation, and/or sealing of tissue, e.g., blood vessels and/or other tissue structures. The generator may include a plurality of outputs for interfacing with various ultrasonic and electrosurgical instruments (e.g., ultrasonic dissectors and hemostats, monopolar instruments, return electrode pads, bipolar electrosurgical forceps, footswitches, etc.). Further, the generator may include electronic circuitry configured to generate energy specifically suited for powering ultrasonic instruments and electrosurgical devices operating in various modes (e.g., cut, blend, coagulate, seal, etc.).

Referring to FIG. 1, an energy-based surgical system 100 is shown which may include a plurality of surgical instruments, such as a first electrosurgical instrument 110, a second electrosurgical instrument 120, and an endoscope 130. The first and second surgical instruments 110 and 120 may be monopolar, bipolar, or hybrid (monopolar and bipolar) instruments. The first instrument 110, for example, may be a hybrid instrument and may include a pair of jaws, each having an electrode and used as bipolar forceps, and an extendible monopolar electrode for monopolar treatment.

The second instrument 120 may include a storage 122, which may be a non-volatile memory, which does not require power supply to maintain the stored information. The stored information may include a lookup table storing correspondence between activation periods and angles between two jaw members of the instrument 120. The correspondence may be predetermined based on previously performed surgical operations.

In aspects, the second instrument 120 may be an ultrasonic instrument e.g., vessel sealer/dissector and include an end effector 125. Further, the ultrasonic instrument 120 may include a transducer (not shown), which conveys mechanical ultrasonic motions through the end effector 125 to a surgical site (e.g., tissue).

The endoscope 130 may be an endoscopic camera that is coupled to an endoscope controller 140, which provides light through a fiberoptic cable. The first and second instruments 110 and 120 are coupled to an energy generator 150. The endoscope controller 140 and the energy generator 150 are disposed in a control tower 160. A display 170 may be disposed in the control tower 160, may be a touchscreen, and is configured to output the video feed from the endoscope 130 as well as various graphical user interfaces (GUIs). In aspects, the endoscope controller 140 may provide visible, infrared, laser, or any other suitable light including one or more frequencies of interest, and the endoscope 130 may capture light reflected from the surgical site including the first or second instrument 110 or 120.

The energy-based surgical system 100 may also include a computing device 180, which is in wired or wireless communication with the first and second instruments 110 and 120 and the endoscope 130. The computing device 180 is capable of receiving data from the first and second instruments 110 and 120, e.g., parameters of the first and second instruments 110 and 120, and video data from the endoscope 130. Due to substantial advancement in the communication speed and processing power, the computing device 180 may process the video data substantially at the same time upon reception of the video data. Further, the computing device 180 may be capable of providing desired parameters in real time to the first and second instruments 110 and 120 to facilitate feedback-based control of the surgical operation.

Figure 2:
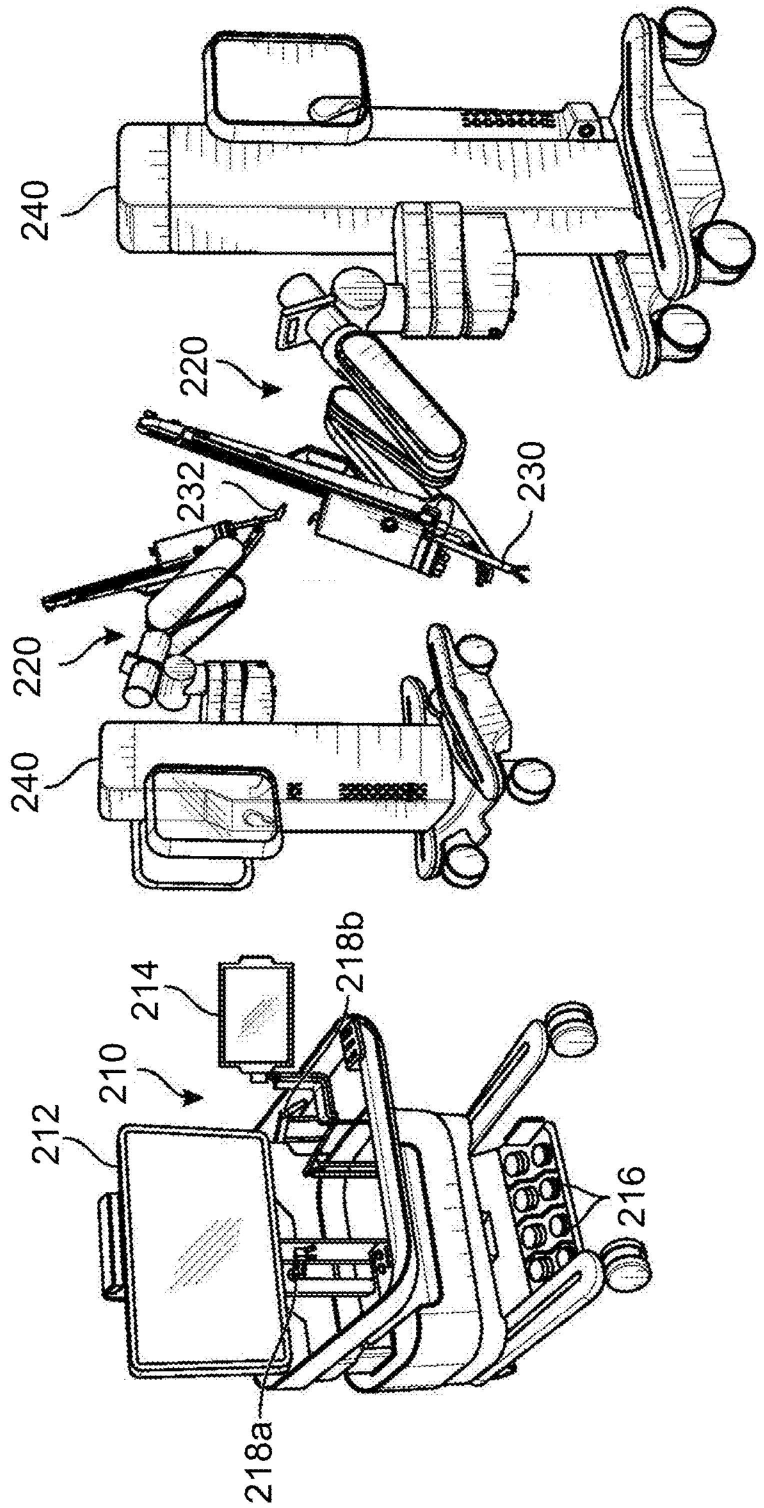
FIG. 2 is a perspective view of a surgical robotic system for use with the energy-based surgical system of FIG. 1 according to various aspects of the present disclosure.

With additional reference to FIG. 2, a surgical robotic system 200 is shown. The energy-based surgical system 100 of FIG. 1 may be used as part of the surgical robotic system 200. The control tower 160 may be also connected to one or more of the components of the surgical robotic system 200, which includes a surgical console 210 and one or more robotic arms 220. Each of the robotic arms 220 may include a surgical instrument 230 (e.g., one of the first or second instruments 110 and 120) removably coupled thereto. Each of the robotic arms 220 may be also coupled to a movable cart 240.

A camera 232 (e.g., the endoscope 130 of FIG. 1) may be coupled to one of the robotic arms 220. The camera 232 is configured to capture live images (e.g., video stream) of the surgical site. The surgical console 210 may include a first display 214, which displays a video feed of the surgical site provided by the camera 232, and a second interaction display 214, which displays a user interface for controlling the surgical robotic system 200. The first and second displays 212 and 214 may be touchscreens allowing for displaying various graphical user interfaces and receiving inputs from users.

The surgical console 210 may include a plurality of user interface devices, such as pedals 216 and a pair of handle controllers 218*a* and 218*b*, which are used by a user to remotely control robotic arms 220. The surgical console 210 may further include an armrest used to support clinician's arms while operating the handle controllers 218*a* and 218*b*.

The control tower 160 may act as an interface between the surgical console 210 and one or more robotic arms 220. In particular, the control tower 160 is configured to control the robotic arms 220, such as to move the robotic arms 220 and the corresponding surgical instruments 230, based on a set of programmable instructions and/or input commands from the surgical console 212, in such a way that the robotic arms 220 and the surgical instruments 230 execute a desired movement sequence in response to input from the foot pedals 216 and the handle controllers 218*a* and 218*b*.

Each of the control tower 160, the surgical console 210, and the robotic arms 220, which are interconnected to each other using any suitable communication network based on wired or wireless communication protocols, may include a respective computing device (e.g., the computing device 180 of FIG. 1). The term "network," whether plural or singular, as used herein, denotes a data network, including, but not limited to, the Internet, Intranet, a wide area network, or a local area networks, and without limitation as to the full scope of the definition of communication networks as encompassed by the present disclosure. The computing devices of the robotic system 200 and the endoscope controller 140 may include any suitable processor (not shown) operably connected to a memory (not shown).

Figure 3:
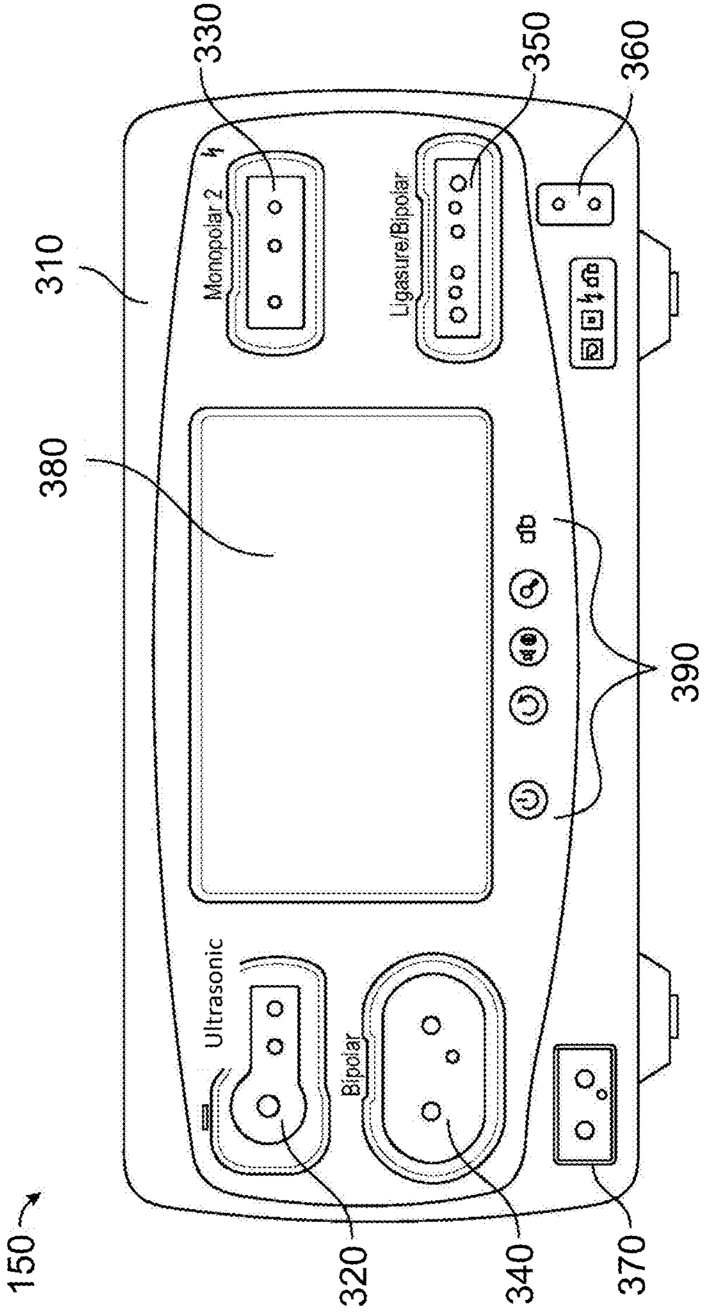
FIG. 3 is a front view of the energy generator of FIG. 1 according to various aspects of the present disclosure.

With reference to FIG. 3, a front face 310 of the generator 150 of FIG. 1 is shown according to various aspects of the present disclosure. The generator 150 may include a plurality of ports 320, 330, 340, 350 to accommodate various types of instruments, a port 360 for coupling to a return electrode pad, and a port 370 configured to couple to a footswitch. The port 330 is configured to couple to monopolar electrosurgical instruments (e.g., the monopolar portion of first instrument 110 of FIG. 1). The ports 340 and 350 are configured to couple to bipolar electrosurgical instruments (e.g., the bipolar portion of the first instrument 110 of FIG. 1). The port 320 is configured to couple to ultrasonic surgical instrument (e.g., the second instrument 120 of FIG. 1). The generator 150 may include a display 380 for providing the user with variety of output information (e.g., intensity settings, treatment complete indicators, etc.). The display 380 may be a touchscreen configured to display a menu corresponding to each of the ports 320, 330, 340, 350 and the instrument coupled. The user also adjusts inputs by touching corresponding menu options. The generator 150 may also include suitable input controls 390 (e.g., buttons, activators, switches, touchscreen, etc.) for controlling the generator 150.

The generator 150 is configured to operate in a variety of modes and is configured to output ultrasonic drive signals (e.g., to power an ultrasonic transducer), monopolar waveforms, and/or bipolar waveforms corresponding to the selected mode. Each of the modes may be activated by the buttons disposed on the first and second instruments 110 and 120.

In aspects, either or both instruments 110 and 120 may be powered by a portable power source and/or a portable generator. For example, with reference to FIGS. 4A and 4B, an ultrasonic surgical device 400 for treating tissue with a portable power source and generator is illustrated. The ultrasonic surgical device 400 includes a power source 410, a housing 430, a transducer 450, and an elongated assembly 490. The power source 410 provides DC power to the transducer 450. In aspects, the power source 410 may be a portable power source, such as a battery, that can be attached to the ultrasonic surgical device 400 to provide DC power at any location. The power source 410 may be insertable or integrated into the housing 430 so that the ultrasonic surgical device 400 may be portably carried without disturbances of any cable. In aspects, the power source 410 may be rechargeable so that the power source 410 may be reusable and so that the ultrasonic surgical device 400 may be disposed at the robotic arm 220 of FIG. 2 without the need for any cable.

In aspects, the power source 410 may include a converter that is connected to an alternating current (AC) power source and converts the AC power to DC power. The AC power source may be of a relatively low frequency, such as about 60 hertz (Hz), while the ultrasonic surgical device 400 operates at a higher frequency. Thus, the power source 410 may convert the low frequency AC power to DC power so that the DC power may then be inverted to AC power having a frequency suitable to cause the transducer 450 to generate ultrasonic mechanical motions.

Figure 4A:
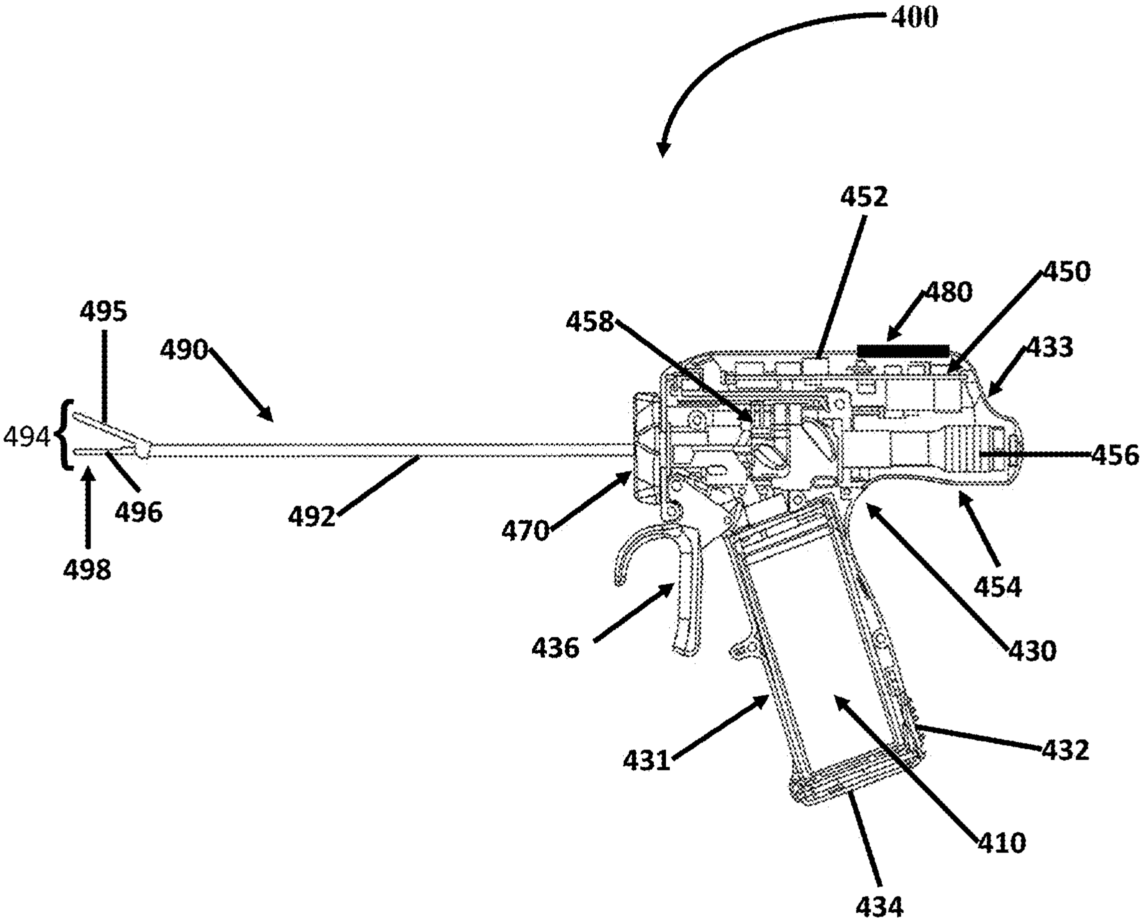
FIG. 4A is a side elevation view of an ultrasonic surgical device according to various aspects of the present disclosure.
Figure 4B:
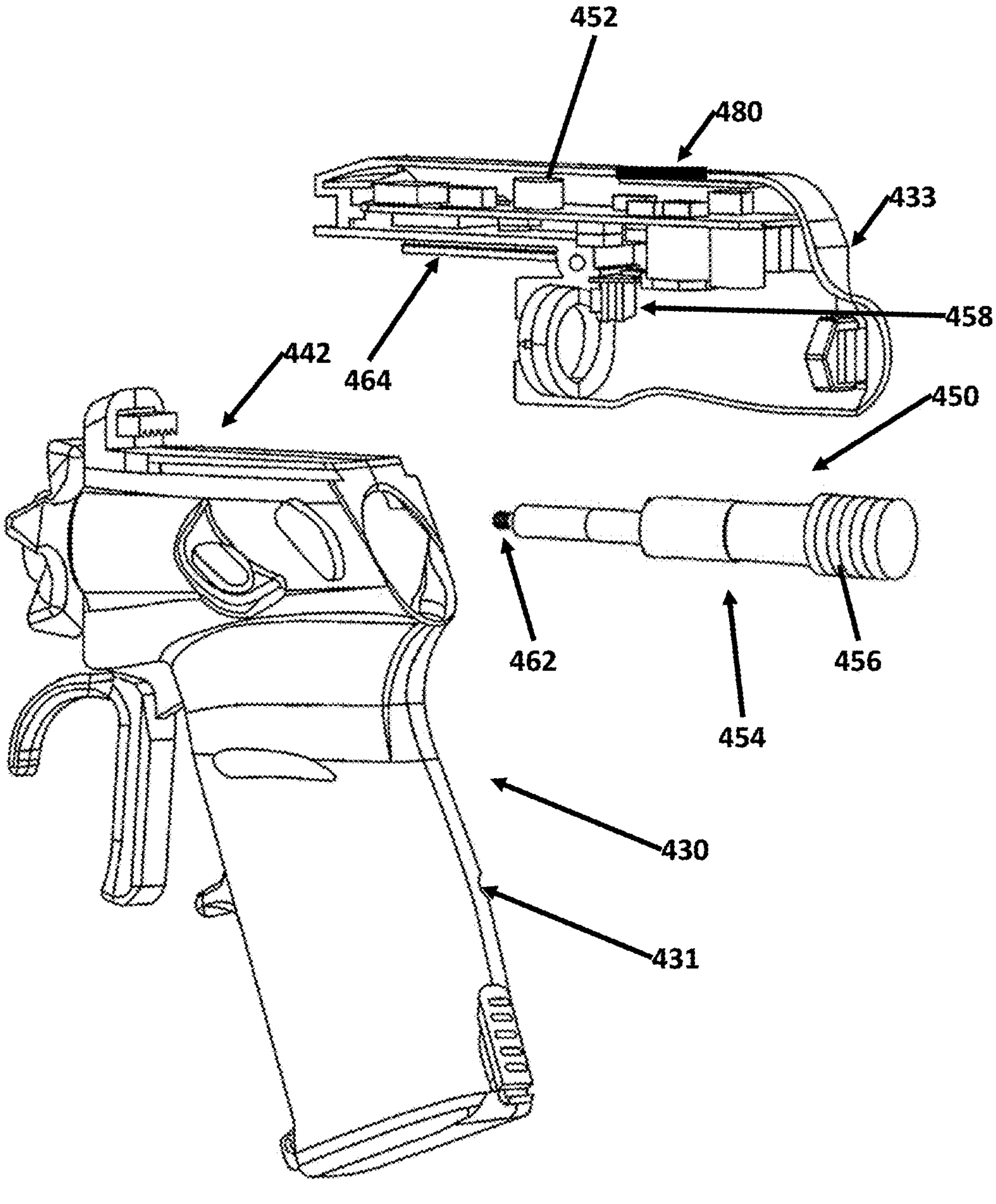
FIG. 4B is a perspective view, with parts separated, of a proximal portion of the ultrasonic surgical device of FIG. 4A according to various aspects of the present disclosure.

With continued reference to FIGS. 4A and 4B, the housing 430 includes a handle portion 431 having a compartment 432, which may house the power source 410, and a power source door 434 that secures the power source 410 within the compartment 432. In an aspect, the power source door 434 may be configured to form a water-tight, hermetic, or aseptic seal between the interior and the exterior of the compartment 432.

The housing 430 also includes a cover 433, which houses the transducer 450 and an output device 480. The transducer 450 includes a generator assembly 452 and a transducer assembly 454, having a transducer body 456 and a locking portion 462 (FIG. 4B). The generator assembly 452 is electrically coupled to the transducer assembly 454 via a pair of contacts 458.

With reference to FIG. 4B, the transducer 450 is illustrated as being separate from the cover 433. When the transducer 450 is inserted into and assembled with the cover 433, the pair of contacts 458 is connected to the transducer 450 so that the rotational movement of the transducer body 456 does not disrupt the connection between the transducer body 456 and the generator assembly 452. Thus, the transducer body 456 is capable of freely rotating within the housing 430.

The output device 480 outputs information about the ultrasonic surgical device 400 or a status of the mechanical coupling between the elongated assembly 490 and the transducer 450. In various embodiments, the output device 480 may also display a warning that the elongated assembly 490 is not adequately connected to the transducer 450.

The handle portion 431 further includes a trigger 436. When the trigger 436 is actuated, the power source 410 provides energy to the transducer 450 so that the transducer 450 is powered to generate ultrasonic mechanical motions along the elongated assembly 490. As the trigger 436 is released, the power supply to the transducer 450 is terminated.

The generator assembly 452 receives the DC power from the power source 410 and generates AC signals having a frequency greater than 20 kHz. The generator assembly 452 can generate signals having a frequency based on a desired mode of operation, which may be different from the resonant frequency of the transducer 450.

The transducer body 456 of the transducer assembly 454 receives the AC signal generated by the generator assembly 452 and generates ultrasonic mechanical motion along the elongated assembly 490 based on the amplitude and the frequency of the generated AC signal. The transducer body 456 includes one or more piezoelectric elements, which converts the generated AC signal into ultrasonic mechanical motions.

The ultrasonic surgical device 400 also includes a spindle 470, which is coupled to the elongated assembly 490 and allows for rotation of the elongated assembly 490 about its longitudinal axis. The elongated assembly 490 is attached to the housing and is mechanically connected to the transducer 450 via the locking portion 462 such that as the spindle 470 is rotated about the longitudinal axis defined by the elongated assembly 490, the elongated assembly 490 and the transducer 450 are also rotated correspondingly without affecting the connection between the transducer 450 and the elongated assembly 490.

The elongated assembly 490 may include an end effector 494, which includes, a jaw member 495 and a blade 496 suitable for sealing tissue by converting the longitudinal mechanical movements into heat. The blade 496 extends from the outer driver sleeve 492. The elongated assembly 490 is mechanically coupled to the transducer body 456 via the locking portion 462.

A proximal portion of the outer drive sleeve 492 is operably coupled to the trigger 436 of the handle portion 431, while a distal portion of the outer drive sleeve 492 is operably coupled to the jaw member 495. As such, the trigger 436 is selectively actuatable to move the outer drive sleeve 492 to pivot the jaw member 495 relative to the blade 496 of the end effector 494 from a spaced-apart position to an approximated position for clamping tissue between the jaw member 495 and the blade 496. The spindle 470 is rotatable in either direction to rotate the elongated assembly 490 in either direction relative to the handle portion 431.

The end effector 494 further includes a waveguide 498, which extends through the outer drive sleeve 492. The waveguide 498 defines the blade 496 at a distal end thereof. The blade 496 serves as the blade of the end effector 494. The waveguide 498 is mechanically coupled to the transducer 450 such that ultrasonic motion produced by the transducer 450 is transmitted along the waveguide 498 to the blade 496 for treating tissue clamped between the blade 496 and the jaw member 495 or positioned near the blade 496.

The jaw member 495 may be formed as a pivoting arm configured to grasp and/or clamp tissue between the jaw member 495 and the blade 496. When the jaw member 495 and the blade 496 grasp tissue and the blade 496 conveys the ultrasonic mechanical motions, temperature of the grasped tissue between the blade 496 and the jaw member 495 increases due to the ultrasonic mechanical motions. These motions in turn treat, e.g., cuts and/or seals, the tissue. In accordance with an aspect of the present disclosure, as detailed below, the blade 496 may vibrate at an appropriate velocity based on a size of the tissue, e.g., blood vessel, to be sealed.

In aspects, by controlling the velocity of the mechanical motions of the blade 496, the heating rate of the tissue, e.g., vessel, may be controlled so that the vessel can be effectively sealed. For example, in aspects, the heating rate may be maintained to be a constant initial heating rate for an initial period of time until a particular amount of energy is supplied to the vessel, and then the heating rate may be changed to a heating rate curve until completion of the sealing of the vessel. The constant initial heating rate and/or the heating rate curve may vary depending on the size of the vessel. Further, the initial time period and the following time period until completion of the sealing may vary depending on the size of the vessel.

Figure 5:
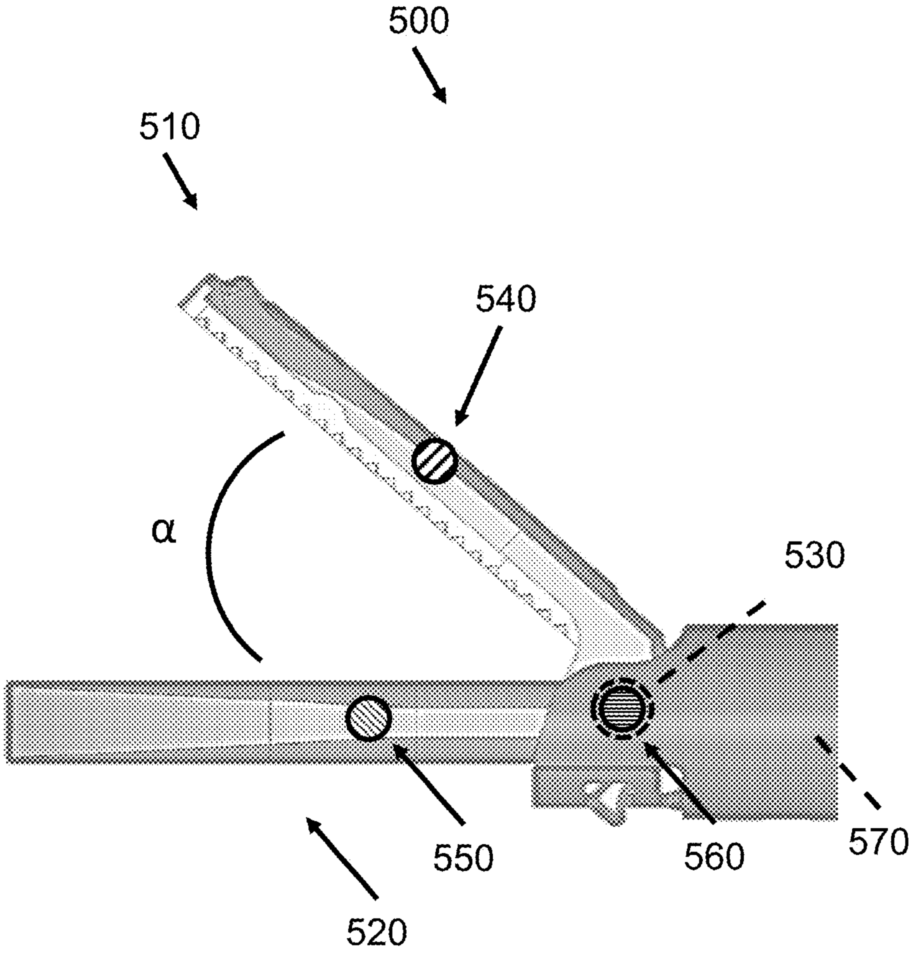
FIG. 5 is an enlarged, side view of a distal portion of an ultrasonic instrument according to various aspects of the present disclosure.

With reference to FIG. 5, an expanded view of the distal portion of an end effector 500 of an ultrasonic surgical instrument (e.g., the end effector 494 of FIG. 4A or the end effector of the instrument 120 of FIG. 1) is shown. The end effector 500 includes a blade 520 and a jaw member 510, which may rotate about a pivot 530 so that the jaw member 510 and blade 520 are capable of grasping tissue therebetween. When electrical waveforms are supplied to the transducer, e.g., transducer 454 of the ultrasonic instrument 400 (FIGS. 4A-4B), the transducer 454 converts the electrical waveform into mechanical movements, which are delivered through a waveguide 570 of the end effector 500 to the blade 520, thereby causing the blade 520 to vibrate and generate heat. Thus, when the tissue is grasped between the jaw member 510 and the blade 520 or adjacent to the blade 520, the tissue may be sealed or dissected based on the velocity of vibration of the blade 520.

The size of the tissue is an important factor in determining the appropriate velocity of the blade 520 to achieve a desired effect, e.g., sealing. Although the size of the tissue is not typically known, it can be estimated based on an angle $\alpha$. That is, when grasping tissue between the blade 520 and the jaw member 510, angle $\alpha$ is defined therebetween, which corresponds to the size of the tissue because the larger or the tissue is, the greater the angle $\alpha$ formed between the jaw member 510 and the blade 520.

During a surgical operation inside the body of a patient, a medical professional might not be able to directly measure, or it may be impractical and/or time consuming, to manually measure the angle $\alpha$ or otherwise estimate the size of the tissue. Thus, the angle $\alpha$ may instead be measured or calculated by performing image processing on the video data from the endoscope 130 of FIG. 1. The video data may capture the surgical site and the distal portion of the end effector 500. Depending on the viewing direction of the endoscope 130 toward the end effector 500 and the distance between the endoscope 130 and the end effector 500, it is a challenge to accurately measure the angle α. Thus, to increase accuracy in calculation of the angle α, three or more markers may be attached to several distal portions of the end effector 500. In aspects, a first marker 540 may be attached on the jaw member 510, a second marker 550 may be attached on the blade 520, and a third marker 560 may be attached at the pivot 530. Each of the first, second, and third markers 540-560 may include a respective predetermined pattern thereon so that accurate identification of locations of each marker can be increased. The predetermined patterns on the end effector 500 may be distinct from each other and may not be affected by the viewing angle or the distance.

In an aspect, markers' exact locations may not be of interest on the condition that one marker is located on the stationary portion (e.g., the blade 520) of the end effector 500 about the pivot 530 and one marker is located on moving portion (e.g., the jaw member 510) of the end effector 500 about the pivot 530.

In another aspect, the first marker 540 may include an additional redundant marker nearby, and the third marker 560 may include an additional redundant marker nearby. In a further aspect, a fourth marker may be disposed on the waveguide 570 or a shaft of the ultrasonic surgical instrument. Since the jaw member 510 and the blade 520 are frequently occluded by tissue, four markers including first to third markers 540-560 and the fourth marker may enhance accurate estimation of the angle α.

As an alternative to markers 540-560, sensors may be utilized in some, all, or different positions as markers 540-560 to enable angle detection. Such sensors may include, for example, Hall-effect sensors, other electrical/magnetic proximity sensors, optical sensors, flexible angle sensors, etc. Now referring back to FIG. 1, the computing device 180 may perform image processing on video data transmitted from the endoscope 130. Further, a current ultrasonic energy level of the ultrasonic instrument 120 or 400 may also be transmitted to the computing device 180. Then, the computing device 180 calculates a desired energy level of the ultrasonic instrument 120 or 400 based on the video data and the current energy level, and transmits the desired energy level to the ultrasonic instrument 120 or 400. In particular, the desired energy level may be calculated based on the angle between the jaw member and the blade of the ultrasonic instrument 120 or 400. In turn, the ultrasonic instrument 120 or 400 may perform a closed-loop control to follow the desired energy level to achieve a desired surgical effect, e.g., tissue sealing.

In aspects, the initial angle may be used to infer an initial size of the tissue. Thus, based on the initial angle, the computing device 180 may determine an initial desired ultrasonic energy level. After the initial measurement of the angle, when the current angle is greater than the previous angle, the desired energy level may be set to be greater than the current energy level. Expansion of the angle occurs when water components in the tissue are heated up and are evaporated and the pressure in the tissue is correspondingly increased, thereby increasing the angle. On the other hand, when the current angle becomes less than the previous angle, the desired energy level may be set to be less than or equal to the current energy level. Contraction of the angle occurs when the pressure built up in the tissue exits, as steam, allowing the tissue to shrink, thereby decreasing the angle. In aspects, when the angle turns from expansion to contraction, the corresponding temperature at the tissue may be the ideal temperature for tissue sealing. Thus, a desired energy level corresponding to the turning point angle may be set as the desired energy level. This energy level, in turn, corresponds to an ideal tissue sealing temperature for the particular tissue being treated.

In aspects, the computing device 180 may perform one or more algorithms for processing the video data to determine the angle. The algorithm(s) may include one or more artificial intelligence algorithms which may include machine learning algorithms or combination thereof, and which have been trained to estimate an angle and calculate a desired ultrasonic energy level based on the angle. The desired energy level may be calculated based on the video data of previously performed surgeries. For example, the video data may include frame images and tagged information, which are used to train the artificial intelligence algorithm to calculate a desired energy level along the surgery. In an aspect, the tagged information may be manually entered by doctors, experts, or medical professionals of the previous surgeries. Further, the artificial intelligence algorithm may refine or update internal control parameters with video data and associated tagged information of new surgeries.

Regarding the tagged information, doctors or medical professionals may manually tag tools, organs, and progression information of the surgery in each video or in each relevant frame image. Specifically, medical professionals may tag a tool, a size of vessel, an angle between the jaw member 510 and the blade 520 of the end effector 500 of the ultrasonic instrument in each relevant image frame or video, and/or a desired energy level corresponding to the angle. In an aspect, the artificial intelligence algorithm may process frame images or videos of previously performed surgeries and automatically add tagged information. Such tagged information may be reviewed, confirmed, and/or revised by experts, doctors, or medical professionals.

A detailed description of determining an angle between two opposing structures, e.g., a pair of jaw members or a jaw member and a blade, can be found in U.S. Provisional Patent Application Ser. No. 63/155,801, filed on Mar. 3, 2021, the entire contents of which are incorporated herein by reference. Further, determination of the jaw angle is not limited thereto but can be accomplished as detailed in U.S. patent application Ser. No. 16/644,367 filed on Jul. 31, 2020, U.S. patent application Ser. No. 13/736,650 filed on Jan. 8, 2013, now U.S. Pat. No. 8,764,749, and U.S. patent application Ser. No. 15/418,809 filed on Jan. 30, 2017, the entire contents of each of which are incorporated herein by reference.

The above angle determination is not limited to use for determining a size of tissue between a jaw member and a blade in an ultrasonic surgical instrument but may also apply to jaw members of a bipolar electrosurgical forceps or opposing structures of any other suitable surgical device. Likewise, the closed-loop control detailed herein may be utilized for adjusting the energy, selecting an energy profile, adjusting energy delivery parameters, etc., in any suitable surgical instrument, whether mechanical vibration energy, bipolar Radio Frequency (RF) energy, monopolar RF energy, thermal energy, microwave energy, light energy, or other suitable energy, in order to maintain a determined ideal temperature based on the angle.

Figure 6:
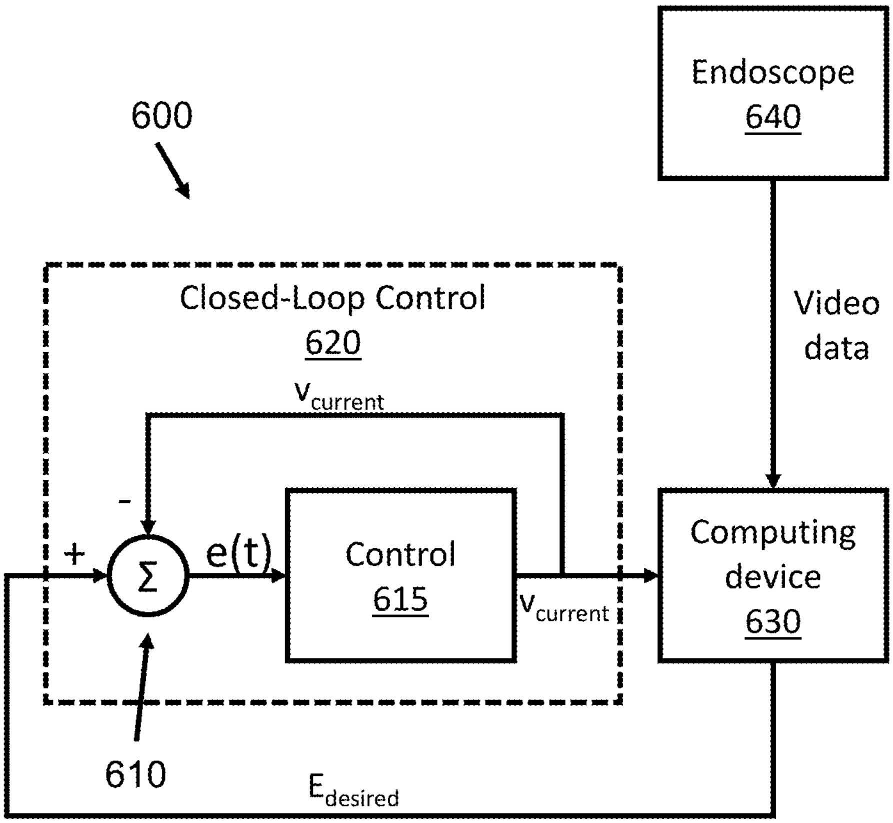
FIG. 6 is a block diagram of a closed-loop control of an ultrasonic instrument according to various aspects of the present disclosure.

With reference to FIG. 6, a block diagram illustrating a closed-loop control or feedback control 620 by an ultrasonic instrument 600, such as any of the ultrasonic surgical instruments detailed herein, is shown. The closed-loop control 620 includes a summer 610 and a control block 615. In a wired or wireless connection, the ultrasonic instrument 600 may be connected to a computing device 630 and the computing device 630 may be connected to an endoscope 640, as similarly described above with respect to the instrument 120 or 500, the endoscope 130, and the computing device 180.

When energized, the ultrasonic instrument 600 may output a current energy level to the computing device 630. The endoscope 640 provides video data, which captures the surgical site including the ultrasonic instrument 600, to the computing device 630. Alternatively, other suitable sensor data may be provided. Based on the video data (or other sensor data), the computing device 630 executes one or more algorithms, which may include one or more artificial intelligence algorithms, to identify/calculate an angle between the opposed structures (e.g., the jaw member and blade) of the ultrasonic instrument 600. In particular, the computing device 630 processes the video data (or other sensor data) and identifies an initial angle when the ultrasonic instrument 600 initially clamps on tissue. In aspects, the computing device 630 may store a lookup table, which shows relationship between angles and corresponding desired energy levels. Thus, based on the initial angle, the computing device 630 is able to determine the size of the tissue and transmit a desired energy level $E_{desired}$ corresponding to the initial angle.

The summer 610 of the closed-loop control 620 subtracts the current energy level from the desired energy level $E_{desired}$ and produces an error, e(t). For example, e(t) may be based on $V_{desired}-V_{current}$, where $V_{desired}$ is a desired velocity of the ultrasonic blade and $V_{current}$ is the current velocity of the ultrasonic blade, and the velocity is one measure of the current energy level. Here, the desired energy level $E_{desired}$ may act as a reference value and a feedback signal to the control 615. At the beginning of the surgical operation, the error e(t) is just the desired energy level $E_{desired}$ because there is no current energy level. However, after the energy is supplied and the blade of the ultrasonic instrument 600 starts vibrating, the ultrasonic instrument 600 starts generating the current energy level.

The vibration of the blade of the ultrasonic instrument 600 generates heat in the grasped tissue and the generated heat causes water components in the tissue to be heated up and evaporated or steamed. Due to the evaporation, the pressure within the tissue increases, thereby increasing the angle from the initial angle. The endoscope 640 captures the increase in the angle in the video data, and the computing device 630 detects the increase in the angle and transmits a new desired energy level $E_{desired}$ corresponding to the change in the angle or a new angle to the ultrasonic instrument 600.

In aspect, the control 615 may utilize a proportional-integral-derivative (PID) or proportional-integral (PI) controller. For example, the PID controller can be expressed as follows:

$$F_{next} = K_p e(t) + K_i \int_0^t e(t)dt + K_d \frac{de(t)}{dt},$$

where $K_p e(t)$, $$K_i \int_0^t e(t)dt,$$

and $$K_d \frac{de(t)}{dt}$$

are proportional, integral, and derivative amounts of the PID control, respectively; $K_p$, $K_i$, and $K_d$ are proportional, integral, and derivative constants, respectively; e(t) is an error between the current energy level and the desired energy level $E_{desired}$ based on the difference between $V_{current}$ and $V_{desired}$; and $V_{next}$ is an energy level of the ultrasonic instrument 600 after performing the PID control. In particular, the proportional constant amplifies the error, e(t), to provide the proportional amount.

$$\int_0^t e(t)dt$$

is the sum of the error over time and provides the accumulated offset, which is then multiplied by the integral constant to provide the integral amount. The derivative of the error, $$\frac{de(t)}{dt},$$

is calculated by determining the slope of the error over time and the derivative term is obtained by multiplying this rate of change by the derivative constant $K_d$. The next energy level based on $V_{next}$ after the PID control is obtained by adding the current energy level based on $V_{current}$ and the sum of the proportional, integral, and derivative amounts.

In aspects, the proportional, integral, and derivative constants, $K_p$, $K_i$, $K_d$, may be predetermined based on data from previous surgical operations. In aspects, the proportional, integral, and derivative constants, $K_p$, $K_i$, $K_d$, may be updated or refined to fine-tune the energy level so that the ultrasonic instrument 600 may maintain the ideal temperature to facilitate tissue sealing.

After the pressure inside the tissue decreases to the external pressure, the steam built up inside the tissue is released from the tissue and the jaw angle starts decreasing. The temperature, at which the jaw angle turns from expansion to contraction, as noted above, may be the ideal temperature to form a tissue seal. The jaw angle between the expansion and the contraction may be a target angle. The computing device 630 may transmit the desired energy level $E_{desired}$ corresponding the target angle (and ideal temperature) to the ultrasonic instrument 600 so that the temperature at the grasped tissue may be maintained at the ideal temperature, e.g., by adjusting blade velocity, activation duration, turning the supply of energy on and off intermittently, and/or in any other suitable manner.

In aspects, the ultrasonic instrument 600 may include a lookup table, which is stored in a memory therein. The look-up table may include predetermined correspondences between activation (activation velocity, remaining activation time, ON/OFF periods, etc.) and angles of the ultrasonic instrument 600. Thus, when the computing device 630 sends the angle to the ultrasonic instrument 600 with the desired energy level $E_{desired}$ based on $V_{desired}$, the ultrasonic instrument 600 may activate vibrations corresponding to the angle. During activation, the desired energy level $E_{desired}$ based on $V_{desired}$ may be maintained as the reference energy level and is used in the PID control 620 while updating the current energy level based on $V_{current}$ of the ultrasonic instrument 600.

Figure 7:
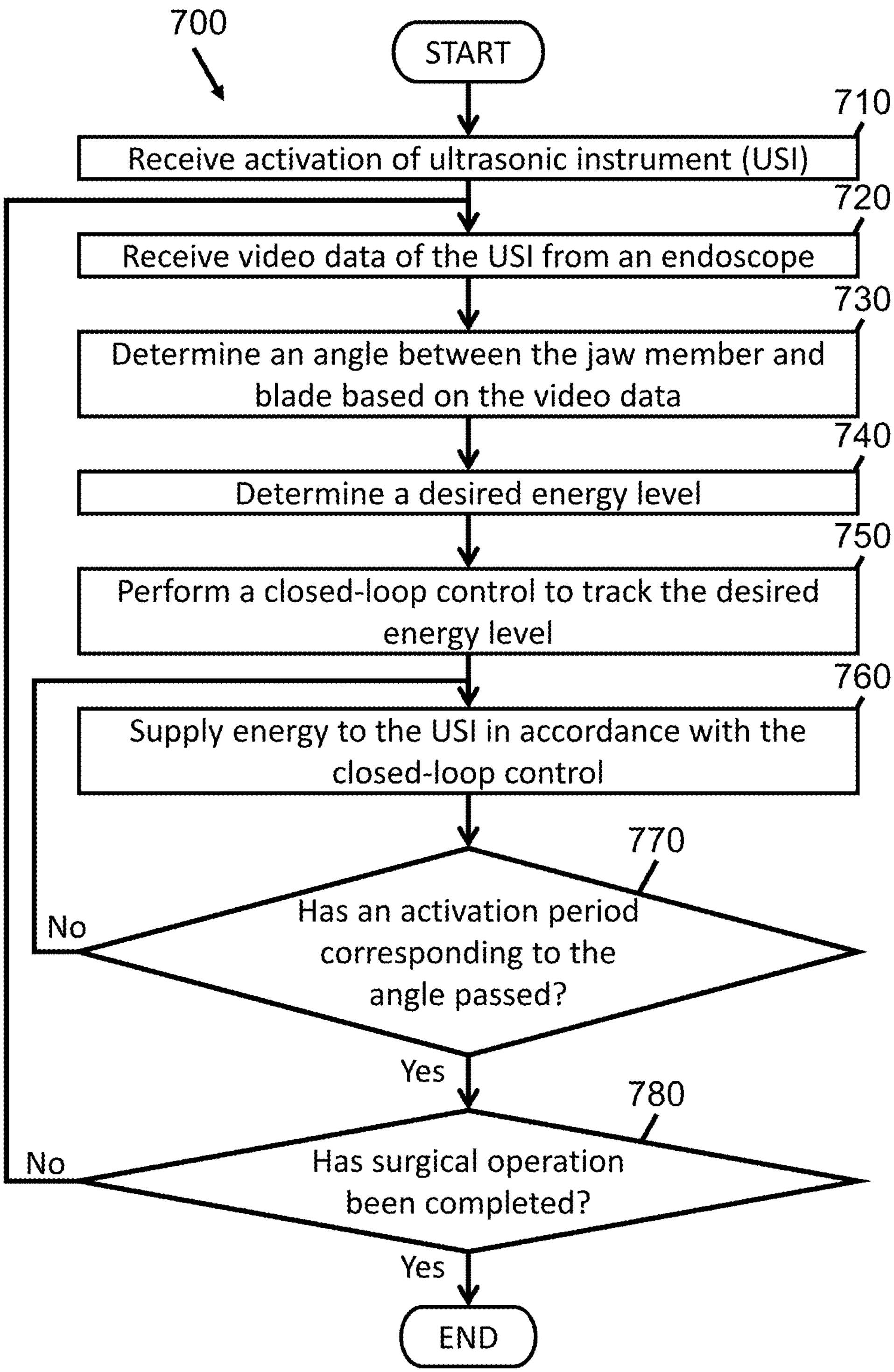
FIG. 7 is a flow chart of a method for a closed-loop control of an ultrasonic instrument according to various aspects of the present disclosure.

Now referring to FIG. 7, a method 700 for performing a closed-loop control for an ultrasonic instrument is shown. The method 700 is started when the ultrasonic instrument is activated. Such activation is received by a computing device in step 710. An endoscope, which is separate from the ultrasonic instrument, may generate video data capturing a surgical site including a distal portion of the ultrasonic instrument; the computing device also receives the video data in step 720. In aspects, the video data and the activation may be received at the substantially same time. As an alternative to video data, other sensor data indicative of an angle of the end effector of the ultrasonic instrument may be obtained and supplied to the computing device.

The computing device may execute one or more algorithms, e.g., including one or more artificial intelligence algorithms, to determine an angle between the jaw member and blade of the ultrasonic instrument based on the video data from the endoscope in step 730. Extremely low-latency in wireless communication among the computing device, the endoscope, and the ultrasonic instrument, and fast identification of the angle by the algorithms enables a real-time control, in aspects. Further, the computing device may determine a desired energy level for the ultrasonic instrument based on the angle in step 740.

The desired energy level is transmitted to the ultrasonic instrument, which then performs a closed-loop control based on the desired energy level in step 750. The closed-loop control may be a PI control, PID control or a cascade of PI or PID controls. The desired energy level may function as a feedback to the closed-loop control so that the closed-loop control may track the desired energy level.

In aspects, the computing device may also transmit, in step 740, the angle and the desired energy level to the ultrasonic instrument, which stores a lookup table including relationship between activation and angles. Energy is continued to be supplied to the ultrasonic instrument in step 760 according to the determined activation corresponding to the received angle, e.g., at the appropriate velocity for the appropriate duration, with or without intermittent ON/OFF, etc. It is then determined whether or not the activation duration or period, has passed in step 770. If not, the supply of energy is continued in step 760, until the corresponding activation period ends.

When it is determined that the corresponding activation period has ended in step 770, it is also determined whether or not the surgical operation has been completed in step 780. When it is determined that the surgical operation has not been completed in step 780, steps 720-780 are repeated until the surgical operation is completed. When it is determined that the surgical operation has been completed, energy may be terminated, or a different energy may be supplied. For example, when it is determined tissue has been sealed, a tissue cutting energy may subsequently be delivered.

With respect to other forms of energy, e.g., RF energy, energy delivery duration, ON/OFF pulsing, etc., may also be controlled based on the angle and other feedback information, e.g., temperature information from one or more temperature sensors included in the end effector or associated with another surgical device within the surgical field, in order to achieve an effective tissue seal for the particular tissue.

Figure 8:
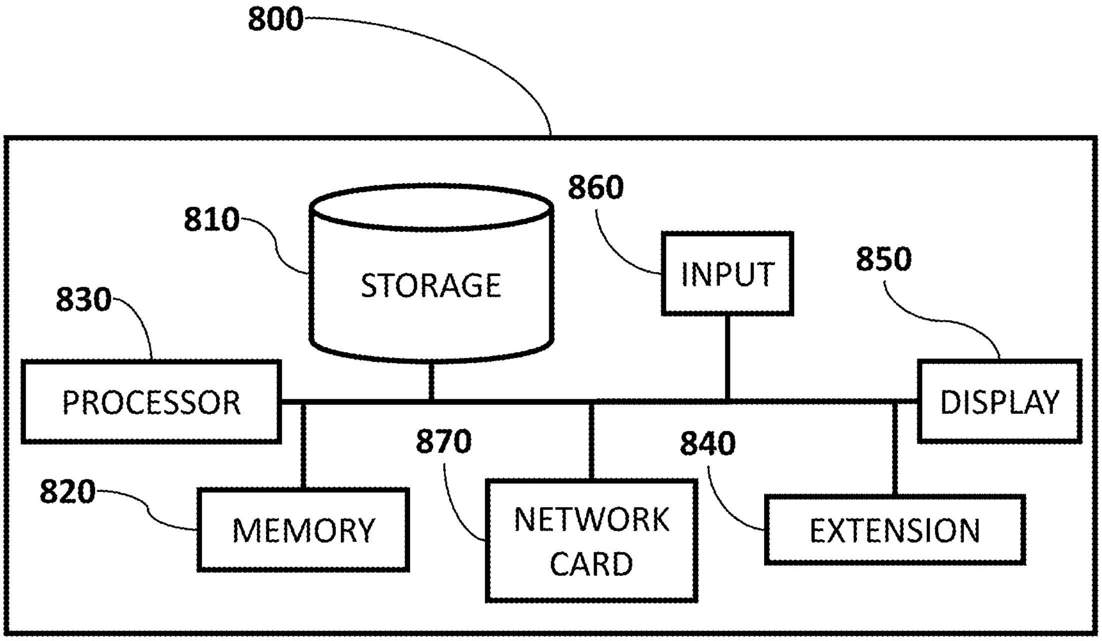
FIG. 8 is a block diagram of a computing device according to various aspects of the present disclosure.

Now referring to FIG. 8, a block diagram of a computing device, which is representative of the computing device 180 of FIG. 1, is shown. The computing device 800 may include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, embedded computers, and the likes. Those of skill in the art will recognize that many smartphones are suitable for use in the system described herein. Suitable tablet computers include those with booklet, slate, and convertible configurations, known to those of skill in the art.

In aspects, the computing device 800 includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, Novell® NetWare®, and the likes. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In aspects, the operating system may be provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

The computing device 800 includes a storage 810. In aspects, the storage 810 may be one or more physical apparatus used to store data or programs on a temporary or permanent basis. The storage 810 may be volatile memory, which requires power to maintain stored information, or non-volatile memory, which retains stored information even when the computing device 800 is not powered. In aspects, the non-volatile memory includes flash memory, dynamic random-access memory (DRAM), ferroelectric random-access memory (FRAM), and phase-change random access memory (PRAM). In aspects, the storage 810 may include, by way of non-limiting examples, CD-ROMs, DVDs, flash memory devices, magnetic disk drives, magnetic tapes drives, optical disk drives, solid-state drive, universal serial bus (USB) drive, and cloud computing-based storage. In aspects, the storage 810 may be any combination of storage media such as those disclosed herein.

The computing device 800 further includes a processor 830, an extension 840, a display 850, an input device 860, and a network interface 870. The processor 830 is a brain to the computing device 800. The processor 830 executes instructions which implement tasks or functions of programs. When a user executes a program, the processor 830 reads the program stored in the storage 810, loads the program on the RAM, and executes instructions prescribed by the program.

The processor 830 may include a field programmable gate array (FPGA), a digital signal processor (DSP), a central processing unit (CPU), a microprocessor, application specific integrated circuit (ASIC), and combinations thereof, each of which includes electronic circuitry within a computer that carries out instructions of a computer program by performing the basic arithmetic, logical, control and input/output (I/O) operations specified by the instructions. Those skilled in the art will appreciate that the processor may be substituted for by using any logic processor (e.g., control circuit) adapted to execute algorithms, calculations, and/or set of instructions described herein.

In aspects, the extension 840 may include several ports, such as one or more USBs, IEEE 1394 ports, parallel ports, and/or expansion slots such as peripheral component interconnect (PCI) and PCI express (PCIe). The extension 840 is not limited to the list but may include other slots or ports that can be used for appropriate purposes. The extension 840 may be used to install hardware or add additional functionalities to a computer that may facilitate the purposes of the computer. For example, a USB port can be used for adding additional storage to the computer and/or an IEEE 1394 may be used for receiving moving/still image data.

In aspects, the display 850 may be a cathode ray tube (CRT), a liquid crystal display (LCD), or light emitting diode (LED). In aspects, the display 850 may be a thin film transistor liquid crystal display (TFT-LCD). In aspects, the display 850 may be an organic light emitting diode (OLED) display. In various aspects, the OLED display is a passive-matrix OLED (PMOLED) or active-matrix OLED (AMOLED) display. In aspects, the display 850 may be a plasma display. The display 850 may be interactive that can detect user interactions/gestures/responses and the like.

A user may input and/or modify data via the input device 860 that may include a keyboard, a mouse, or any other device with which the use may input data. The display 850 displays data on a screen of the display 850. The display 850 may be a touch screen so that the display 850 can be used as an input device.

The network interface 870 is used to communicate with other computing devices, wirelessly or via a wired connection following suitable communication protocols. Through the network interface 870, the computing device 800 may transmit, receive, modify, and/or update data from and to an outside computing device, server, or clouding space. Suitable communication protocols may include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency—embedded millimeter wave transvers optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, C#, Delphi, Fortran, Java, JavaScript, machine code, operating system command languages, Pascal, Perl, PL1, scripting languages, Visual Basic, meta-languages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

While several aspects of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope of the claims appended hereto.

What is claimed is:

1. An ultrasonic surgical system comprising:

an ultrasonic instrument configured to seal a vessel and including an ultrasonically-activatable blade and a jaw member pivotably movable with respect to the blade;

an endoscope configured to capture video data of a surgical site including the jaw member and the blade of the ultrasonic instrument; and a processor connected to the endoscope and configured to:

process the video data to determine an angle between the jaw member and the blade;

determine a desired ultrasonic energy level based on the angle; and provide the desired ultrasonic energy level as a feedback to the ultrasonic instrument, wherein the ultrasonic instrument performs a closed-loop control to maintain the desired energy level.

2. The ultrasonic surgical system according to claim 1, wherein a first marker is disposed on the jaw member.

3. The ultrasonic surgical system according to claim 2, wherein a second marker is disposed on the blade.

4. The ultrasonic surgical system according to claim 3, wherein a third marker is disposed near a pivot of the ultrasonic instrument.

5. The ultrasonic surgical system according to claim 4, wherein at least one additional marker is disposed near each of the first and third markers.

6. The ultrasonic surgical system according to claim 4, wherein the angle between the blade and the jaw member is determined based on the first, second, and third markers in the captured video data.

7. The ultrasonic surgical system according to claim 6, wherein the angle between the blade and the jaw member is further determined based on the first, second, and third markers and a fourth marker disposed on a shaft of the ultrasonic instrument.

8. The ultrasonic surgical system according to claim 1, wherein the processor is further configured to execute an artificial intelligence algorithm to process the video data.

9. The ultrasonic surgical system according to claim 1, wherein the ultrasonic instrument includes a memory storing predetermined activation periods corresponding to angles between the jaw member and the blade.

10. The ultrasonic surgical system according to claim 9, wherein the angle together with the desired ultrasonic energy level is provided to the ultrasonic instrument.

11. The ultrasonic surgical system according to claim 10, wherein supply of the energy is turned off after an activation time corresponding to the angle has passed.

12. The ultrasonic surgical system according to claim 1, wherein the processor is further configured to control a velocity of the blade based on the desired ultrasonic energy level.

13. The ultrasonic surgical system according to claim 1, wherein the closed-loop control is a proportional-integral (PI) control, proportional-integral-derivative (PID) control, or a cascade of PI or PID controls.

* * * * *